United States Patent
Whalen, II et al.

(10) Patent No.: US 7,374,568 B2
(45) Date of Patent: May 20, 2008

(54) METHODS FOR EMBOLIZING ANEURYSMAL SITES WITH A HIGH VISCOSITY EMBOLIZING COMPOSITION

(75) Inventors: Thomas J. Whalen, II, Encinitas, CA (US); Earl Slee, Laguna Niguel, CA (US); Amanda Conner, Rancho Santa Margarita, CA (US)

(73) Assignee: Micro Therapeutics, Inc., Irvine, CA (US)

( * ) Notice: Subject to any disclaimer, the term of this patent is extended or adjusted under 35 U.S.C. 154(b) by 319 days.

(21) Appl. No.: 10/345,127

(22) Filed: Jan. 14, 2003

(65) Prior Publication Data

US 2003/0223955 A1 Dec. 4, 2003

Related U.S. Application Data

(60) Provisional application No. 60/347,342, filed on Jan. 14, 2002.

(51) Int. Cl.
*A61M 29/00* (2006.01)

(52) U.S. Cl. .................................... 606/194
(58) Field of Classification Search ...................... None
See application file for complete search history.

(56) References Cited

U.S. PATENT DOCUMENTS

| | | | |
|---|---|---|---|
| 4,938,763 A | 7/1990 | Dunn et al. | |
| 5,580,568 A | 12/1996 | Greff et al. | |
| 5,667,767 A * | 9/1997 | Greff et al. | 424/9.411 |
| 5,695,480 A | 12/1997 | Evans et al. | |
| 5,830,178 A | 11/1998 | Jones et al. | |
| 6,296,604 B1 | 10/2001 | Garibaldi et al. | |

FOREIGN PATENT DOCUMENTS

| | | |
|---|---|---|
| WO | 00/71170 A1 | 11/2000 |
| WO | 00/71197 | 11/2000 |

OTHER PUBLICATIONS

"Detachable Coil Embolization" downloaded from the world wide web on Feb. 26, 2007.*
"Aneurysm Embolization" downloaded from the world wide web on Feb. 26, 2007.*
Amdur et al., Casarett and Doull's Toxicology, Editors, Pergamon Press, New York, pp. 661-664 (1975).
Kinugasa, M.D., Kazushi et al., "Direct thrombosis of aneurysms with cellulose polymer," 77 J. Neurosurg pp. 501-507 (1992).

(Continued)

*Primary Examiner*—Michael P. Woodward
*Assistant Examiner*—Eric E. Silverman
(74) *Attorney, Agent, or Firm*—Foley & Lardner LLP

(57) ABSTRACT

Novel methods for embolizing blood vessels which are particularly suited for treating aneurysms are provided. The presently disclosed methods provide for the embolization of aneurysms wherein occlusion of the neck of the aneurysm during embolization by a flow arresting device such as balloon is not required. In one embodiment, the compositions employed in the methods of this invention comprise a biocompatible polymer, a biocompatible solvent and a biocompatible contrast agent wherein the viscosity of this composition is at least about 1000 centistokes at 40° C. and, preferably, at least about 2500 centistokes at 40° C.

11 Claims, 19 Drawing Sheets

OTHER PUBLICATIONS

Kinugasa, M.D., Kzaushi et al. "Early treatment of subarachnoid hemmorrhage after preventing rerupture of an aneurysm," 83 J. Neurosurg. pp. 34-41 (1995).

Kinugasa, M.D., Kzaushi et al. "Prophylactic Thrombosis to Prevent New Bleeding and to Delay Aneurysm Surgery," 36 Neurosurgery 661-667 (1995).

Mandai, Shinya et al., "Direct thrombosis of aneurysms with cellulose acetate polymer," 77 J. Neurosurg. pp. 497-500 (1992).

Taki, M.D., Waro et al., "Select and combination of various endovascular techniques in the treatment of giant aneurysms," 77 J. Neurosurg. pp. 37-42 (1992).

* cited by examiner

METHODS FOR EMBOLIZING ANEURYSMAL SITES WITH A HIGH VISCOSITY EMBOLIZING COMPOSITION

CROSS-REFERENCE TO RELATED APPLICATIONS

This application claims the benefit under 35 U.S.C. §119 (e) of U.S. Provisional Application Ser. No. 60/347,342 filed on Jan. 14, 2002 which application is incorporated herein by reference in its entirety.

BACKGROUND OF THE INVENTION

1. Field of the Invention

This invention is directed to novel methods for embolizing blood vessels which are particularly suited for treating aneurysms.

REFERENCES

The following publications are cited in this application as superscript numbers:

1. Mandai, et al., "Direct Thrombosis of Aneurysms with Cellulose Acetate Polymer", *J. Neurosurg.*, 77:497-500 (1992)
2. Kinugasa, et al., "Direct Thrombosis of Aneurysms with Cellulose Acetate Polymer", *J. Neurosurg.*, 77:501-507 (1992)
3. Casarett and Doull's *Toxicology*, Amdur et al., Editors, Pergamon Press, New York, pp. 661-664 (1975)
4. Greff, et al., U.S. Pat. No. 5,667,767 for "Novel Compositions for Use in Embolizing Blood Vessels", issued Sep. 16, 1997
5. Greff, et al., U.S. Pat. No. 5,580,568 for "Cellulose Diacetate Compositions for Use in Embolizing Blood Vessels", issued Dec. 3, 1996
6. Kinugasa, et al., "Early Treatment of Subarachnoid Hemorrhage After Preventing Rerupture of an Aneurysm", *J. Neurosurg.*, 83:34-41 (1995)
7. Kinugasa, et al., "Prophylactic Thrombosis to Prevent New Bleeding and to Delay Aneurysm Surgery", *Neurosurg.*, 36:661 (1995)
8. Taki, et al., "Selection and Combination of Various Endovascular Techniques in the Treatment of Giant Aneurysms", *J. Neurosurg.*, 77:37-42 (1992)
9. Evans, et al., U.S. patent application Ser. No. 08/655,822 for "Novel Compositions for Use in Embolizing Blood Vessels", filed May 31, 1996
10. Dunn, et al., U.S. Pat. No. 4,938,763 for "Biodegradable In-Situ Forming Implants and Methods of Producing Same", issued Jul. 3, 1990
11. Greff, et al., U.S. Pat. No. 5,695,480 for "Novel Embolizing Compositions", issued Dec. 9, 1997
12. Greff, et al., U.S. Pat. No. 5,830,178 for "Novel Methods for Embolizing Vascular Sites with an Embolizing Composition Comprising Dimethylsulfoxide, issued Nov. 3, 1998.
13. Whalen, et al., International Application Publication No. WO 00/71170 for "Novel High Viscosity Embolizing Compositions", published Nov. 30, 2000.

All of the above references are herein incorporated by reference in their entirety to the same extent as if each individual reference was specifically and individually indicated to be incorporated herein by reference in its entirety.

2. State of the Art

Embolization of blood vessels is conducted for a variety of purposes including the treatment of tumors, the treatment of lesions such as aneurysms, uncontrolled bleeding and the like.

Embolization of blood vessels is preferably accomplished via catheter techniques which permit the selective placement of the catheter at the vascular site to be embolized. In this regard, recent advancements in catheter technology as well as in angiography now permit neuroendovascular intervention including the treatment of otherwise inoperable lesions. Specifically, the development of microcatheters and guide wires capable of providing access to vessels as small as 1 mm in diameter allows for the endovascular treatment of many lesions.

Embolizing compositions heretofore disclosed in the art include those comprising a biocompatible polymer, a biocompatible solvent and a contrast agent which allowed visualization of the in vivo delivery of the composition via fluoroscopy.[1-8] Such compositions typically contain no more than about 8 weight percent of biocompatible polymer based on the weight of the total composition. However, Whalen et al.[13] disclose the use of embolizing compositions comprising up to 50 weight percent of the biocompatible polymer based on the total weight of the composition.

Endovascular treatment regimens preferably include the use of a water insoluble, radiopaque contrast agent in the embolizing compositions in order that the physician can visualize delivery of the composition to the vascular site via conventional techniques such as fluoroscopy.[1-8] Additionally, the use of water insoluble contrast agents is beneficial during post treatment procedures to visualize the embolized mass during, for example, surgery or to monitor the disease condition and/or for retreatment purposes. Visualization is particularly necessary when using catheter delivery techniques in order to ensure both that the composition is being delivered to the intended vascular site and that the requisite amount of composition is delivered. The latter requirement is particularly critical in the treatment of aneurysms where only the aneurysmal sac is intended to be filled while leaving the adjoining blood vessel unaffected. Accordingly, in such treatments, the amount of embolic composition delivered is selected to substantially fill but not overflow the aneurysmal sac. If less than this amount of embolic composition is delivered to the aneurysmal sac, the patient will be left with an active aneurysm which, in some cases, may grow or enlarge. If more than this amount of embolic composition is delivered, the composition will overflow into the adjoining blood vessel which can then embolize this blood vessel as well as the aneurysm. In the case where the affected blood vessel is in or leads to a critical body organ, e.g., the brain, permanent damage due to ischemia will result.

When delivered by catheter, the embolic compositions preferably comprise a biocompatible solvent, a biocompatible polymer and the water insoluble contrast agent.[9-12] The biocompatible solvent is miscible or soluble in blood or other body fluid and also solubilizes the biocompatible polymer during delivery. The biocompatible polymer is selected to be soluble in the biocompatible solvent but insoluble in blood or other body fluid. The water insoluble contrast agent is suspended in the composition and, as above, permits the physician to fluoroscopically visualize catheter delivery of this composition. Upon contact with the blood or other body fluid, the biocompatible solvent dissipates from the embolic composition, whereupon the biocompatible polymer precipitates in the presence of the water insoluble contrast agent and embolizes the blood vessel.

In practice, complications have hindered the delivery of the embolic composition into vascular sites. Previously, low viscosity embolic compositions which flow through catheters at moderate pressures have been used. In many circumstances, a contiguous or ball shape precipitate formed at the ejection port is desired (e.g., to fill an aneurysm). However, low viscosity embolic compositions may not form a dense compact embolizing mass proximate to the ejection port of the catheter; rather a precipitate with string-like characteristics is formed. When exposed to flowing vascular fluid and/or currents within an aneurysm sac, such a stringy precipitate formed from low viscosity embolizing compositions can migrate to form precipitates distal to the catheter ejection port. Distal solidification of a string shape precipitate makes site specific delivery of the solid mass in the vasculature difficult. As is apparent, site specific delivery of the solid mass is essential for treatment of vascular disorders such as aneurysms. Solidification at points distal to the ejection port, as is common in string shape precipitates, can detrimentally result in the solid mass forming not in the aneurysm sac but in the artery attendant the aneurysm. Such a string shape precipitate is more prone to fragmentation which can lead to embolization of this artery and possible incapacitation or death of the patient. Moreover, such fragmentation can lead to particles or fragments being "washed" downstream and lodging at undesired locations in the vasculature.

On the other hand, the use of a flow arresting device to limit blood flow during injection of an embolic composition from a catheter has been suggested.[11] These devices reduce the flow through the artery of aneurysm to be treated, thereby reducing the likelihood of fragments being "washed" downstream.

However, there are severe limitations placed on the use of such devices in combination with embolic compositions delivered via catheters. For example, in situ solidification of embolizing composition is facilitated by removal of the biocompatible solvent from the growing precipitate by blood transport. However, limiting blood flow in the area adjacent the forming precipitate hinders further precipitate formation. In addition, use of flow arresting devices requires additional procedures and equipment resulting in further exposure of the patient to surgical procedures. Moreover, blood flow can be arrested for only a short period of time prior to the onset of tissue damage due to ischemia.

Notwithstanding the benefits associated with the use of embolic compositions in treating aneurysms and other vascular disorders, the art is in search of improved embolization techniques which solve the problems of delivery of a contiguous coherent embolizing mass without the use of flow restriction at the vascular site.

SUMMARY OF THE INVENTION

This invention is directed to novel methods for embolizing blood vessels which are particularly suited for treating aneurysms. These methods, either singularly or in combination, permit the delivery of high viscosity liquid embolic compositions to vascular sites while overcoming one or more of the problems heretofore associated with vascular embolization by use of less viscous compositions. These methods, either singularly or in combination, further permit the controlled, reproducible formation of an embolic precipitate at the vascular site.

In one aspect, the invention is directed to a method for embolizing a vascular aneurysm by delivering to said aneurysm via a catheter having proximal and distal ends a composition comprising (1) a biocompatible polymer; (2) a biocompatible water insoluble contrast agent; and (3) a biocompatible solvent, said method includes:

(a) positioning the distal end of said catheter in said vascular site wherein the proximal end of said catheter is connected to a source of said composition and whereby said composition can be injected into the aneurysm through said catheter; and, (b) injecting a suffient amount of said composition into said aneurysm to embolize said aneurysm;

wherein said composition has a viscosity at about 40° C. of greater than about 1000 centistokes.

The composition preferably has a viscosity at 40° C. of about 1,000 to about 20,000 centistokes; more preferably from about 1000 to 4000 centistokes; even more preferably about 2000 to 3000 centistokes; and most preferably, about 2500 centistokes, although viscosities as low as about 800 centistokes may be used. Particular preferred viscosities at 40° C. include 2300 centistokes, 2500 centistokes and 3200 centistokes.

The viscosity of the composition is such that a compact mass of embolizing precipitate is formed in the aneurysm, preferably in the form of a compact spheroid, and preferably proximate to the distal end of the catheter. The use of a flow arresting device, such as a balloon inflated in the arterial site to seal the neck of an aneurysm, is not required during the injection of the composition, thus no flow arresting device is activated during step (b). The composition is preferably not so viscous that a pressure greater than the burst strength is formed in any component of the apparatus through which the composition is delivered.

In a second aspect, the invention is directed to a method for embolizing a vascular aneurysm by delivering to said aneurysm via a catheter having proximal and distal ends a composition comprising (1) a biocompatible polymer; (2) a biocompatible water insoluble contrast agent; and (3) a biocompatible solvent, said method includes:

(a) positioning the distal end of said catheter in said vascular site wherein the proximal end of said catheter is connected to a source of said composition and whereby said composition can be injected into the aneurysm through said catheter; and, (b) injecting an amount of said composition into the vascular site; and, (c) waiting a sufficient period of time to permit blood flow to transport biocompatible solvent away from the aneurysmal site;

wherein steps (b) and (c) may be repeated until the aneurysm is substantially filled, and wherein said composition has a viscosity at about 40° C. of greater than about 1000 centistokes.

The composition preferably has a viscosity at 40° C. of about 1,000 to about 20,000 centistokes; more preferably from about 1000 to 4000 centistokes; even more preferably about 2000 to 3000 centistokes; and most preferably, about 2500 centistokes, although viscosities as low as about 800 centistokes may be used. Particular preferred viscosities at 40° C. include 2300 centistokes, 2500 centistokes and 3200 centistokes.

The viscosity of the composition is such that a compact mass of embolizing precipitate is formed in the vascular site, preferably in the form of a compact spheroid, and preferably proximate to the distal end of the catheter. The composition is preferably not so viscous that a pressure greater than the burst strength is formed in any component of the apparatus through which the composition is delivered. The use of a flow arresting device, such as a balloon inflated in the arterial site to seal the neck of an aneurysm, is not required during the injection of the composition, thus no flow arresting device is activated during steps (b) and (c). The time waited in step (c) is preferably sufficient for precipitate formation. During this time, a determination of the extent to which the aneurysm has been filled may also be performed.

In a third aspect, the forgoing method may further include the steps of:

(d) after determining that the aneurysm is substantially filled, activating a balloon capable of sealing the aneurysm which is being embolized; and, (e) injecting a final amount of said composition into the aneurysm such the site is completely filled with embolizing composition;

wherein the balloon is inflated proximate to the opening of said aneurysm to a diameter that is about 100% to 130% of the inner diameter of the vascular vessel, and more preferably about 115%.

In further aspects of the invention, any of the forgoing methods may further include: Positioning the distal end of the delivery catheter into a sac to be embolized about ⅔ of the distance between the opening and the fundus. Injecting the biocompatible solvent (e.g., DMSO) into the catheter to fill the lumen of said catheter followed by injecting a first amount of said composition into said catheter whereby at least a portion of said biocompatible solvent is ejected from said catheter into the vascular site and washed downstream therefrom.

BRIEF DESCRIPTION OF THE DRAWINGS

The advantages of the invention will become apparent from the following detailed description of the preferred embodiments thereof in connection with the accompanying drawings, in which.

DETAILED DESCRIPTION OF THE INVENTION

Figure 1:
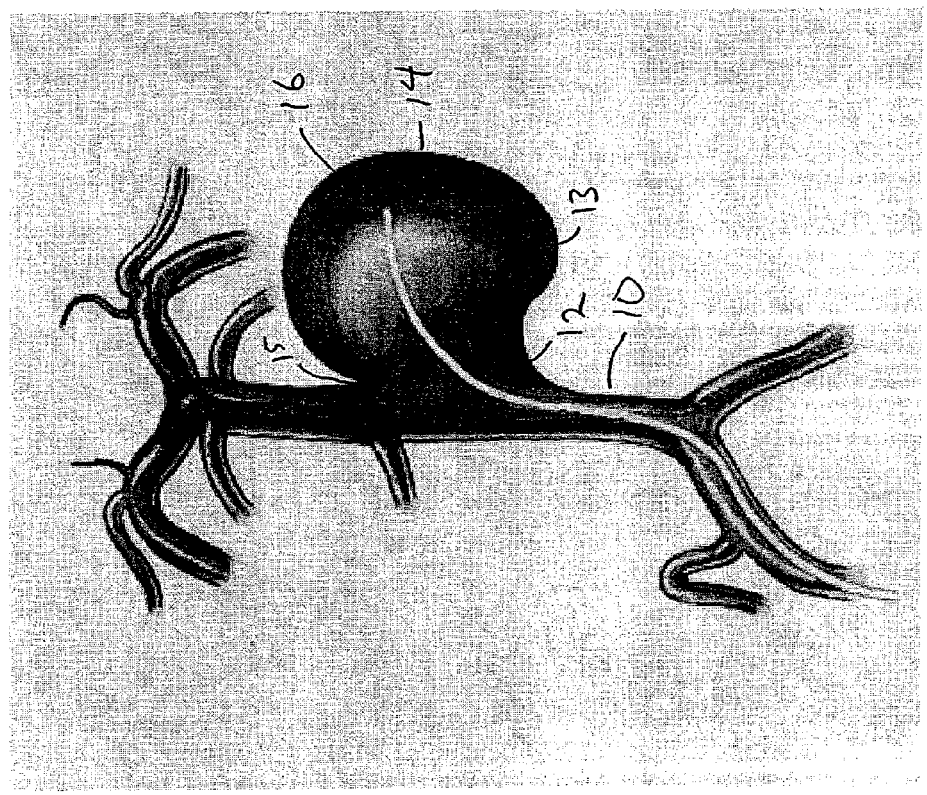
FIGS. 1-5 illustrate an embodiment of the methods of the invention.

This invention is directed to novel methods for embolizing vascular aneurysms by delivering, via catheter, high viscosity embolizing compositions such that the method does not require the use of a flow arresting device proximate to the opening into which the embolizing composition is being injected.

The term "embolizing" refers to a process wherein a material is injected into an aneurysm, fills or plugs the aneurysmal sac and/or encourages clot formation so that blood flow into the aneurysm ceases.

The term "biocompatible polymer" refers to polymers which, in the amounts employed, are non-toxic and substantially non-immunogenic when used internally in the patient and which are substantially insoluble in the body fluid of the mammal. The biocompatible polymer can be either biodegradable or, preferably, non-biodegradable.

The term "contrast agent" refers to a biocompatible radiopaque material capable of being monitored during injection into a mammalian subject by, for example, radiography, real time fluoroscopy, and the like. The contrast agent can be either water soluble or water insoluble. Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, ethyl lactate, dimethylsulfoxide (DMSO), analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

Abbreviations used herein include: mm=millimeter; cm=centimeter; ml=milliliter; psi=pounds per square inch, cSt=centistokes; DMSO=dimethylsulfoxide; and EVOH=ethylene vinyl alcohol copolymer. All temperatures are in degrees Celsius unless otherwise indicated.

Commonly owned U.S. Pat. No. 6,531,111, filed May 19, 2000, incorporated herein in its entirety, describes high viscosity embolizing compositions. These compositions may be adjusted as disclosed therein by one of skill in the art to create embolizing compositions suitable for use in the present invention. One of skill in the art knows how to make alternative formulations which are also suitable for use in the present invention. The primary method for increasing the viscosity of such a composition is to increase the weight percent of the biocompatible polymer in the composition; although, one of skill in the art also knows that modifying other parameters such as increasing the average molecular weight of the biocompatible polymer will increase viscosity.

According to the present invention, a sufficient amount of an embolizing composition is introduced into the selected vascular aneurysm via a catheter delivery means under fluoroscopy so that upon precipitation of the polymer, the aneurysm is embolized. The particular amount of embolizing composition employed is dictated by the total volume of the aneurysmal sac to be embolized, the concentration of polymer in the composition, the rate of precipitation (solids formation) of the polymer, and the like. Such factors are well within the skill of the art.

Delivery of the embolizing compositions to the selected vascular aneurysm is via a medical catheter. The particular catheter employed is not critical provided that catheter components are compatible with the embolizing composition (i.e., the catheter components will not readily degrade in the embolizing composition) and of sufficient strength. Materials compatible with the embolizing compositions can be readily determined by the skilled artisan and include, for example, polyethylene, other polyolefins, fluoropolymers (e.g., Teflon™), silicone, and the like. It is important in practicing the methods of the present invention that the catheter, injection syringe and other portions of the apparatus have sufficient strength to withstand the pressures required to flow a viscous composition through the catheter. The pressure may exceed 2000 pounds per square inch (psi) when using a composition with a viscosity of about 3000 centistokes. Preferably, the catheter, catheter hub and syringe are designed to withstand pressures in excess of 2000 psi. The catheter lumen is preferably maximized so as to reduce the necessary pressure as much as possible. Commonly owned U.S. Pat. No. 6,503,244, issued Jan. 7, 2003, incorporated herein in its entirety, describes high pressure catheters for injecting viscous fluid into the body, and particularly catheters that deliver viscous embolization agents into the vasculature which are suitable for use in the methods of the invention. One of skill in the art will recognize alternative devices and components.

A uniform suspension of contrast agent and biocompatible polymer in the biocompatible solvent is desirable for use in the methods of the invention and may be achieved by heating/mixing the composition at a temperature of above 40° C. which ensures formation of a uniform suspension. The composition may be heated from at least about 3 to about 20 minutes and preferably from about 5-10 minutes to facilitate formation of a uniform suspension. In some cases, the formation of a uniform suspension requires that the heated composition be placed in a suitable mixer, e.g., vortex mixer, and is mixed until the suspension is homogeneous. In this case, after formation of the homogenous suspension via the mixer, the composition is preferably reheated to a temperature of from above about 40° C. to about 90° C. and preferably from about 50° C. to about 70° C. The specific temperature employed for heating is selected relative to the biocompatible solvent and biocompatible polymer employed. Such selections are well within the skill of the art. The heated composition is transferred preferably via a syringe and delivered into the catheter under conditions wherein the temperature of the composition remains above room temperature and preferably above about 40° C. For more information see, for example, U.S. Pat. No. 6,454,738, issued Sep. 24, 2002 which is incorporated herein in its entirety.

As shown in FIG. 1, vascular vessel 10 has an opening 12 that is connected to a sac 13 that forms the aneurysm. The top of the sac is typically referred as the fundus 14 and the base of the sac at the opening is the neck. Standard procedures can be employed to position the distal (i.e., tip) of delivery catheter 16 into the sac. The proximal end of the delivery catheter is connected to one or more syringes.

The method may comprise, for example, the following steps:
1. Place distal tip of the delivery catheter within the aneurysmal site as shown in FIG. 1, preferably about ⅔ into the sac.
2. Flush delivery catheter with saline (e.g., about 5 cc).
3. Fill dead space of delivery catheter with DMSO (e.g., 0.25 cc).
4. Inject a desired amount of embolizing composition (e.g., 0.20 cc) into the delivery catheter channel.
5. Stop injection and wait until the DMSO has been sufficiently flushed from the site (e.g., 1 minute).
6. As illustrated in FIGS. 2-5, slowly inject the embolizing composition until the sac of the aneurysm is filled as visualized by fluoroscopy. A contrast agent can be injected, for example, through a separate catheter proximate to the aneurysm, during the procedure as needed to determine percent of aneurysm fill.
7. The delivery catheter is detached:
   7.1 Wait a sufficient amount of time (e.g, 10 minutes) to permit solidification of the embolizing composition.
   7.2 Aspirate the syringe (e.g., 0.20 cc).
   7.3 Remove slack from the delivery catheter.
   7.4 Detach with quick pull.

Figure 2:
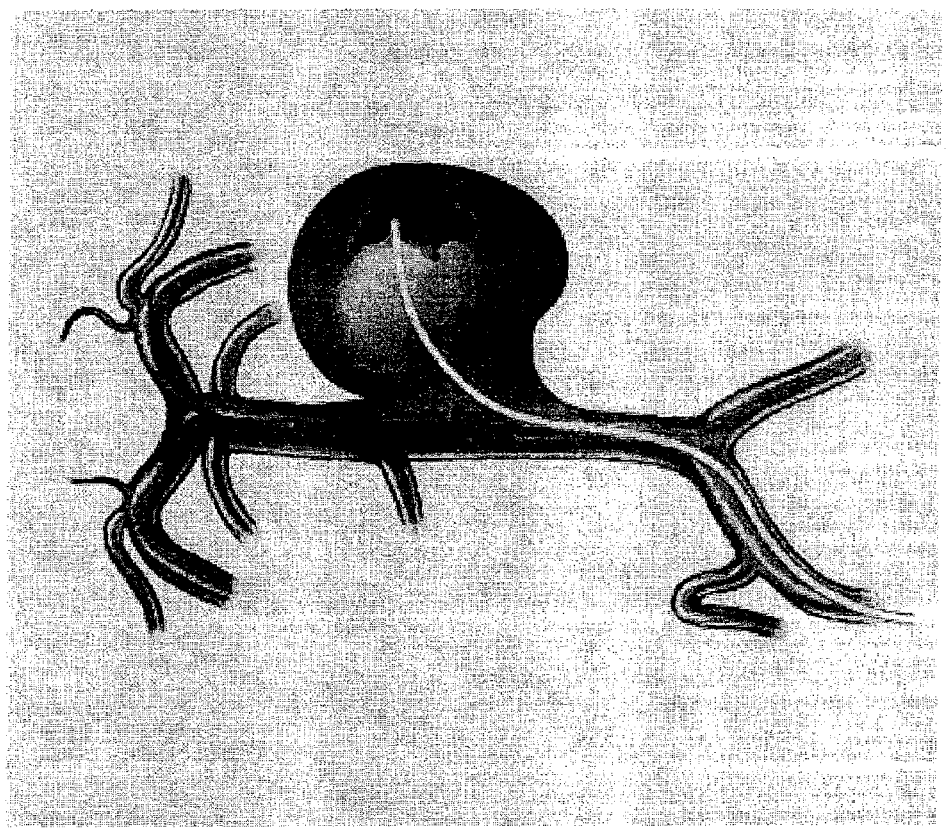
Figure 3:
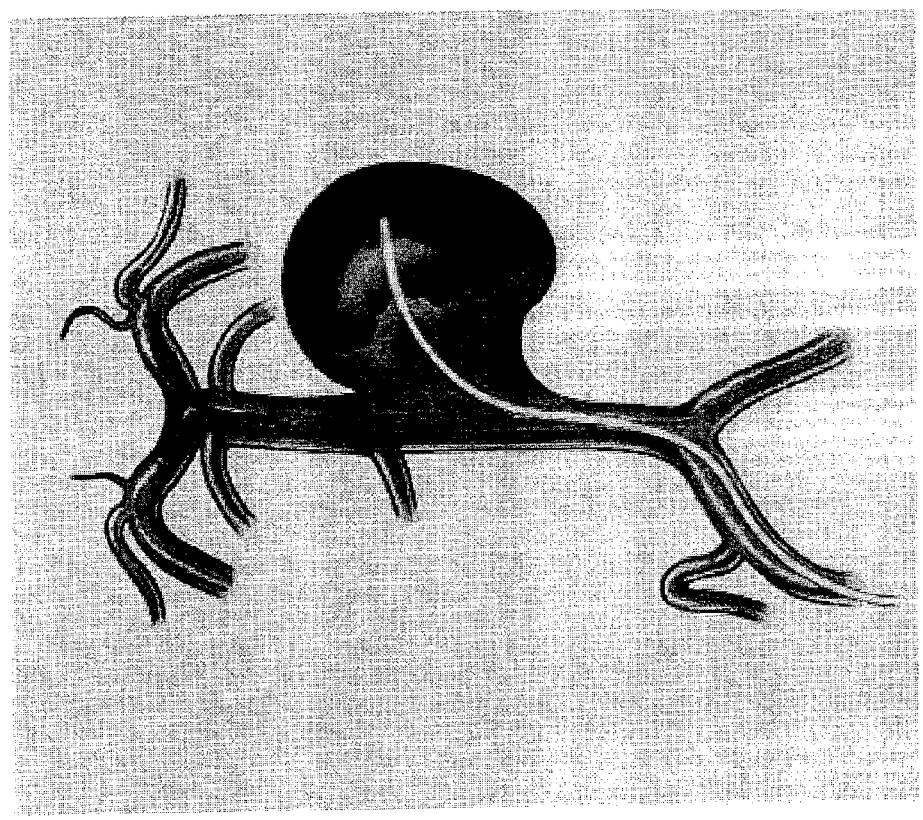
Figure 4:
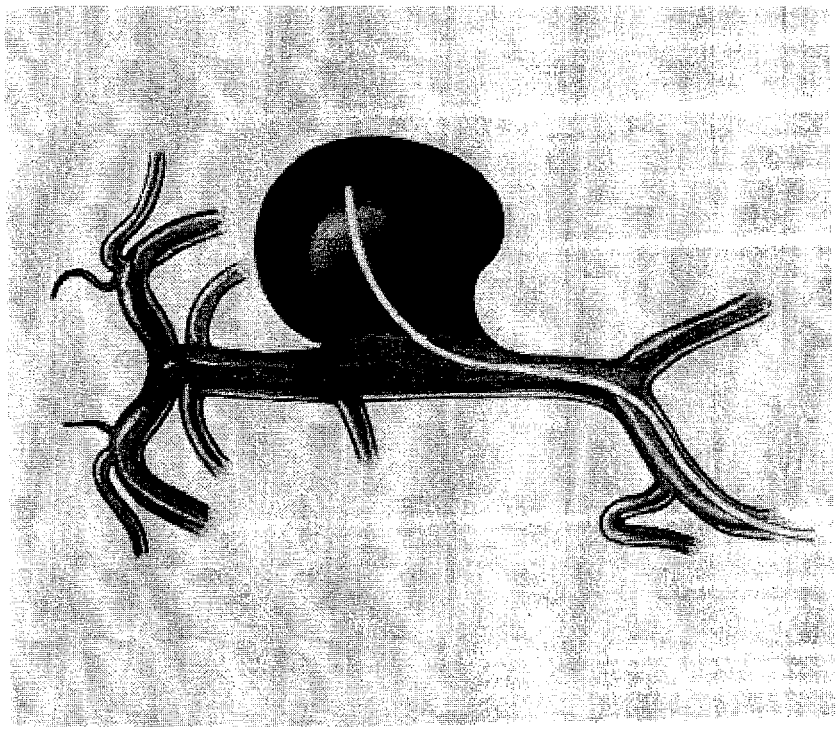
Figure 5:
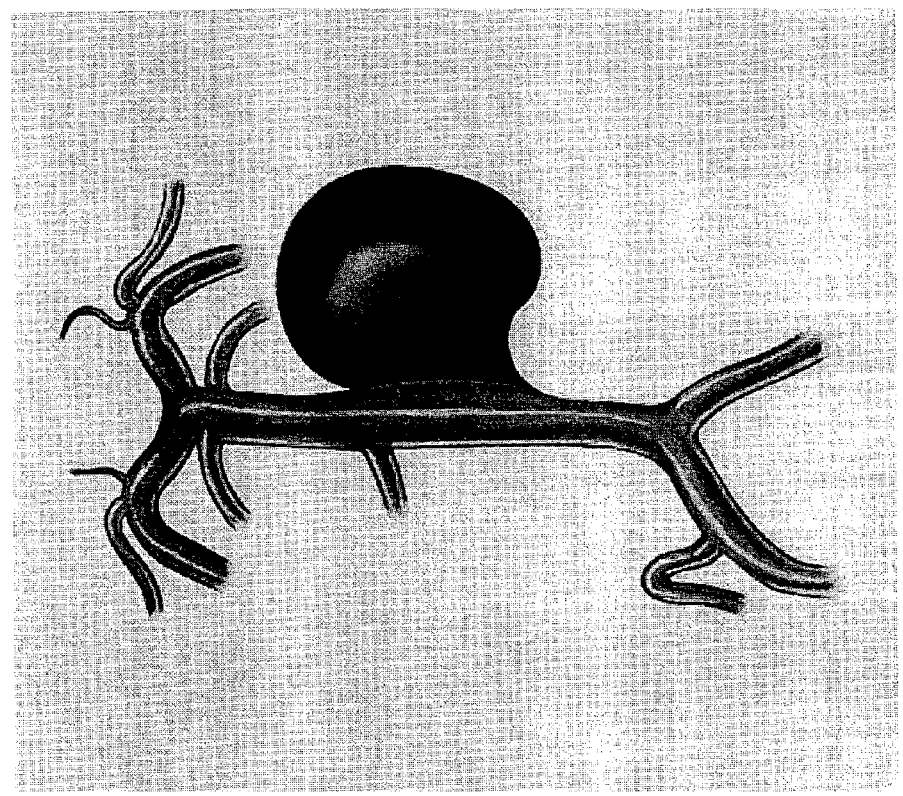
Figure 6:
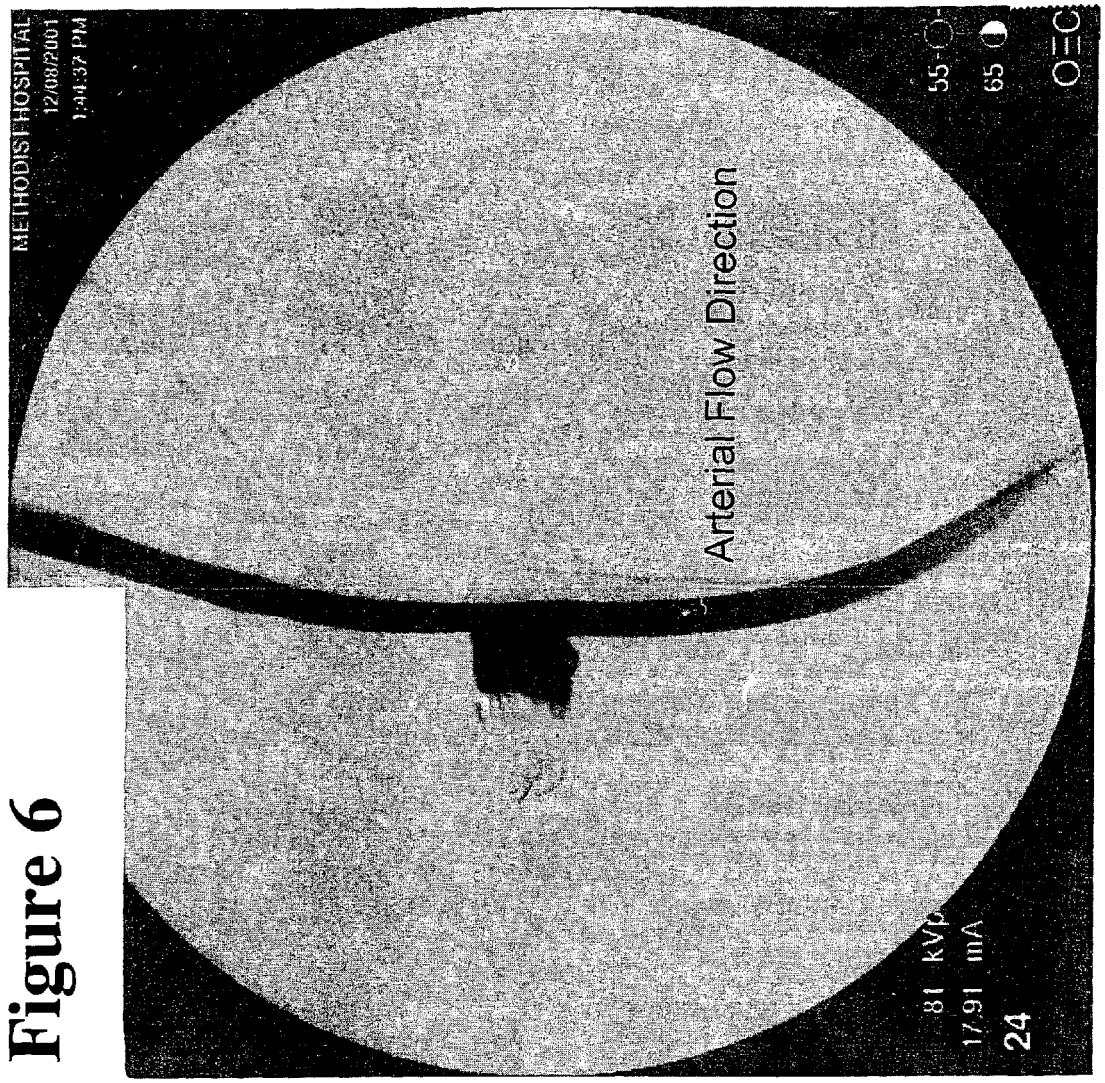
FIGS. 6-11 show fluoroscope images of the embolization of an aneurysm in a porcine subject using the methods of the invention. The embolizing composition had a viscosity at 40° C. of 1000 centistokes. The aneurysm had dimensions 14 mm height, 10 mm sac diameter, and a 6 mm neck diameter.
Figure 7:
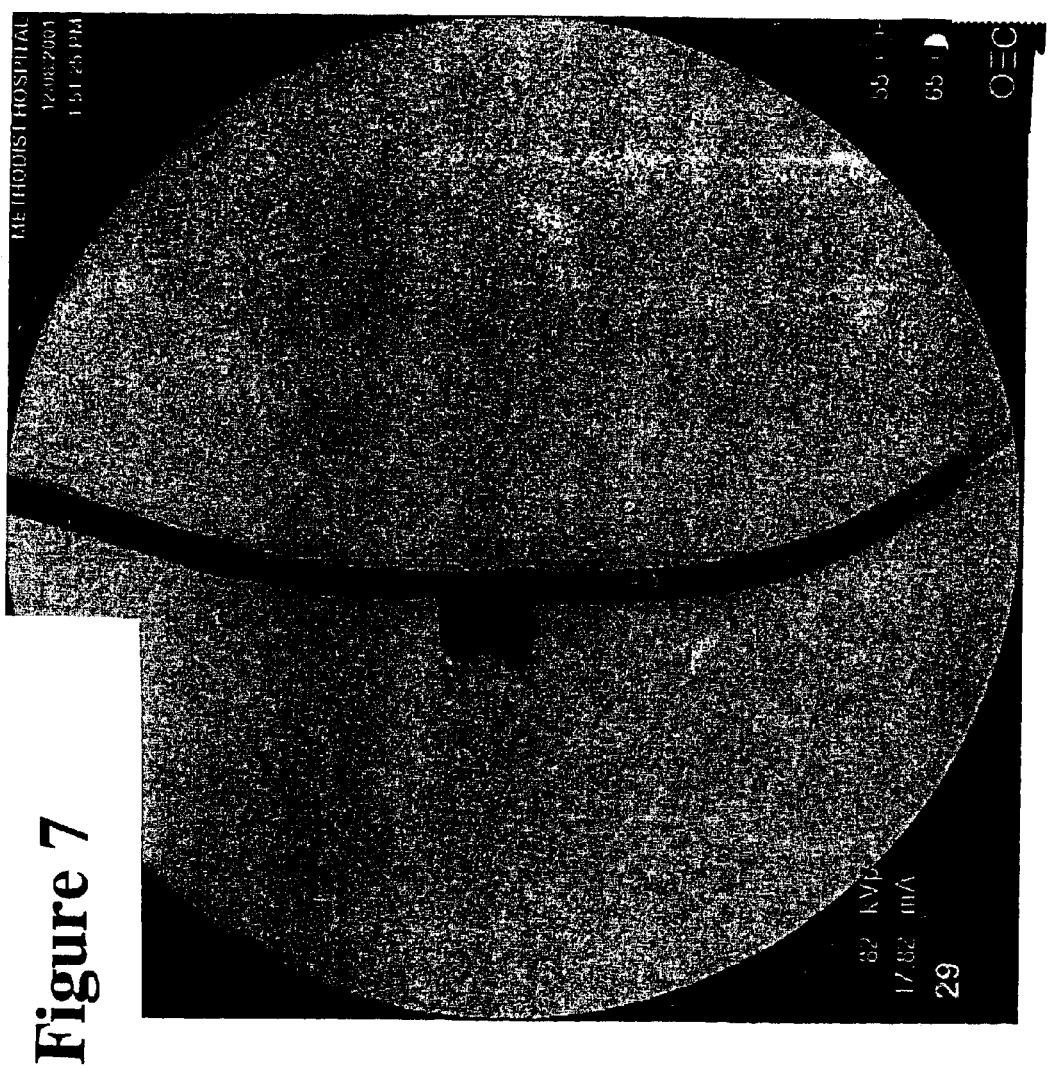
Figure 8:
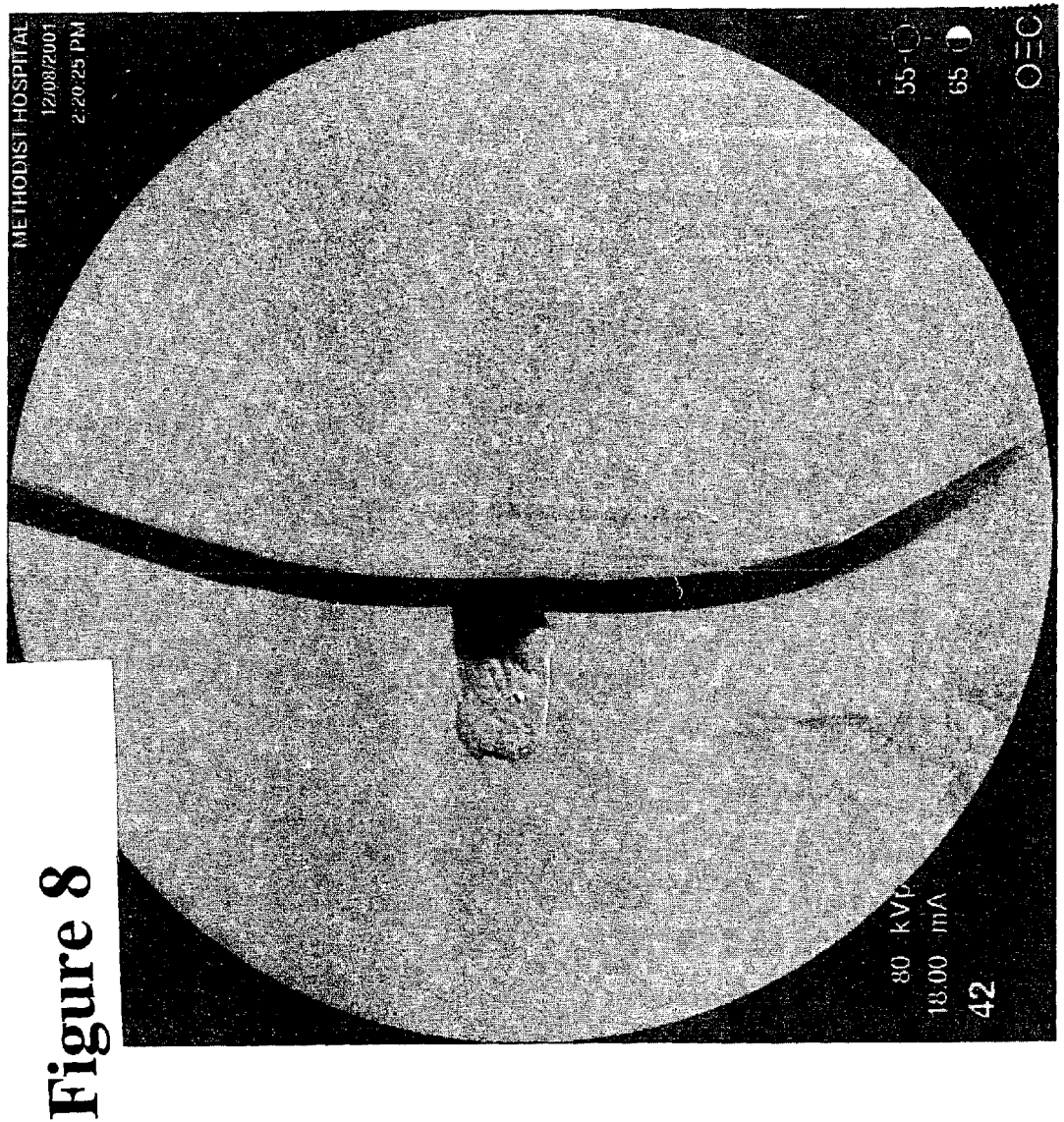
Figure 9:
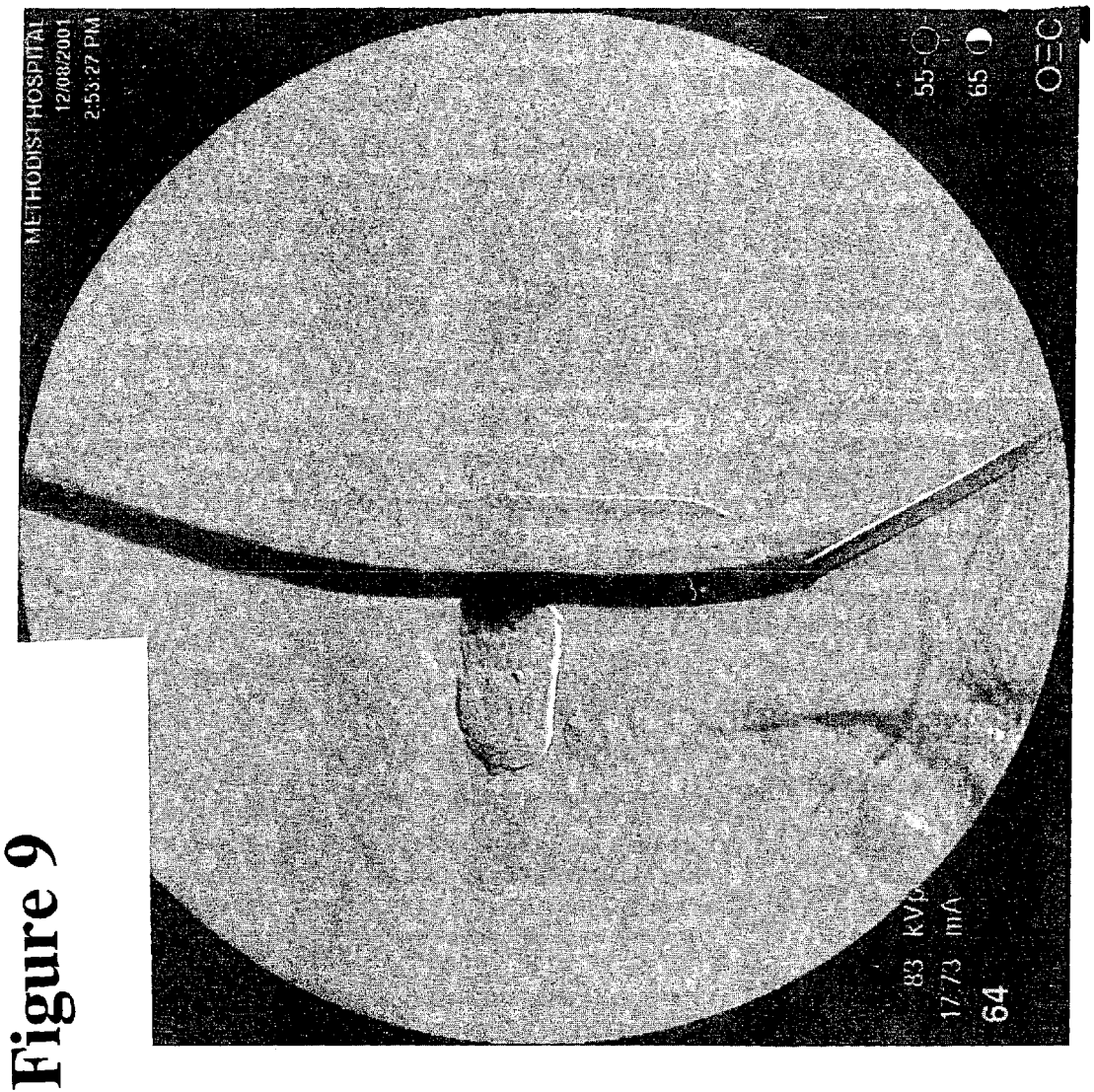
Figure 10:
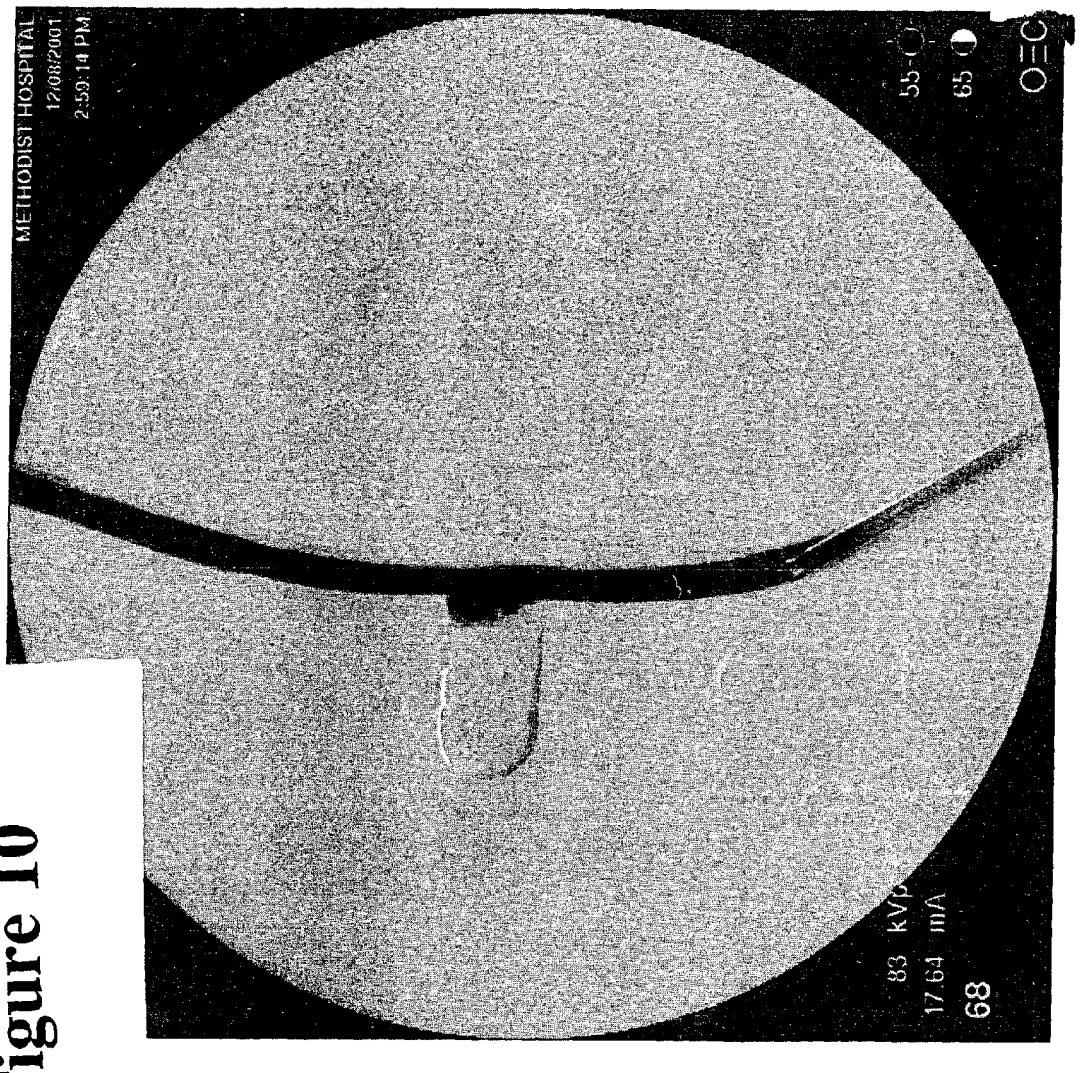
Figure 11:
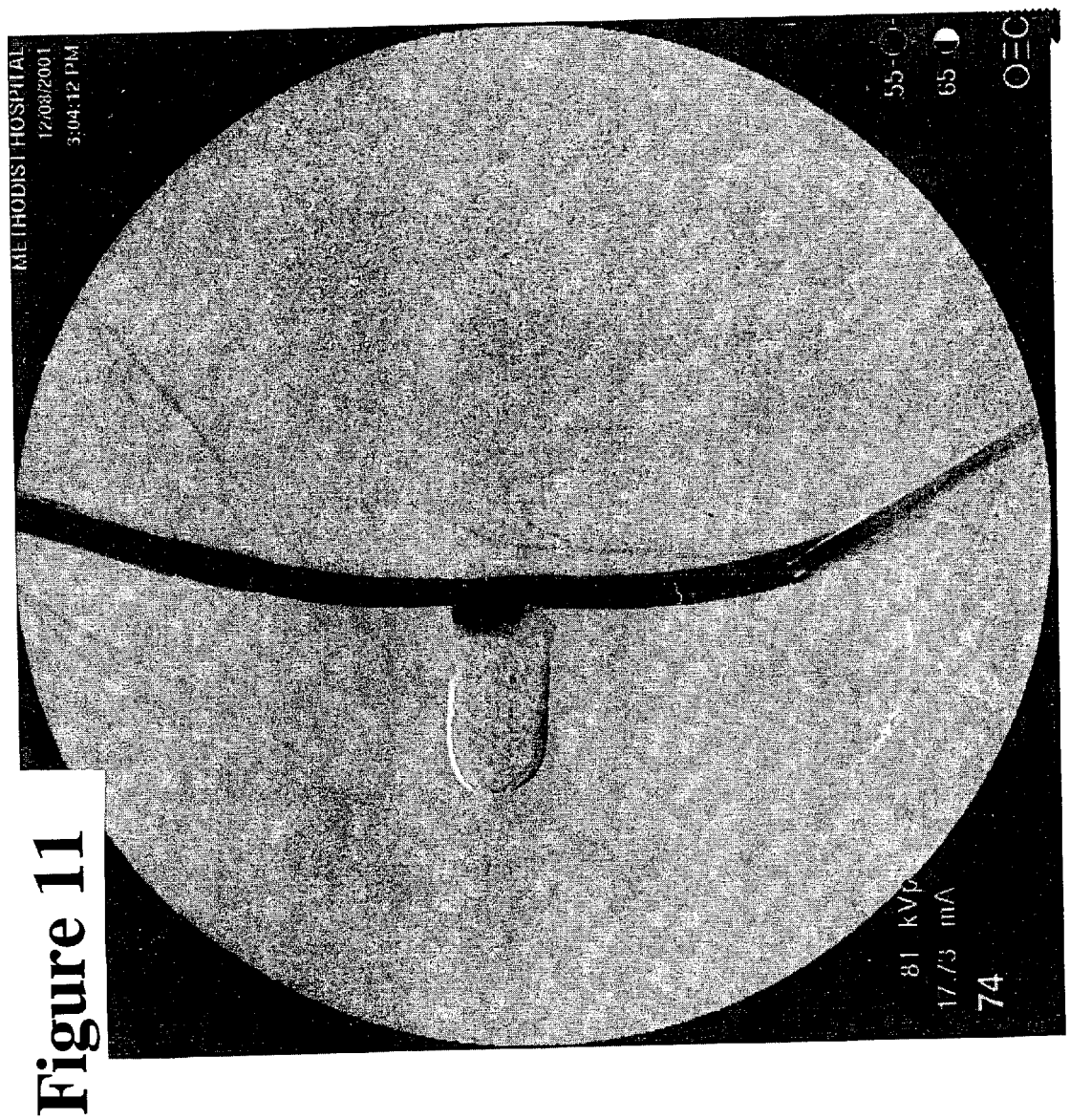

In an alternative embodiment of the invention the above method may be modified as follows, step 6 may comprise some or all of the following sub-steps:
6. Embolize the aneurysm as follows:
   6.1 As shown in FIG. 2, slowly inject the embolizing composition until a nidus forms in the sac of the aneurysm.
   6.2 Wait for a period sufficient to allow perfusion of the site and thereby removal of the biocompatible solvent; this promotes solidification of the precipitate.
   6.3 Slowly inject additional embolizing composition to grow the forming precipitate in the sac of the aneurysm.
   6.4 As shown in FIGS. 3-5, repeat steps 6.2 and 6.3 until the aneurysm is filled as visualized by fluoroscopy. A contrast agent can be used during the procedure as needed to determine extent of aneurysm fill.

During delivery, the catheter is preferably held in place in the aneurysm under conditions which minimize movement of the catheter.

The embolizing composition has a viscosity at 40° C. of at least about 1000 centistokes; preferably from about 1,000 to about 20,000 centistokes; more preferably from about 1000 to 4000 centistokes; even more preferably about 2000 to 3000 centistokes; and most preferably, about 2500 centistokes, although viscosities as low as about 800 centistokes may be used. Particular preferred viscosities at 40° C. include 2300 centistokes, 2500 centistokes and 3200 centistokes. The viscosity is such that the biocompatible polymer precipitate forms a coherent mass at the distal tip of the catheter and does not form strings or similar structures susceptible to breakage. In a preferred embodiment, the viscosity is such that the embolizing material forms a dense spheroidal solid mass within the aneurysm or other vascular site without requiring the use of a flow arresting device. A preferred composition is a high viscosity formulation of the Onxy™ embolizing composition manufactured by Micro-Therapeutics, Inc., Irvine Calif., USA.

A strategy for embolization consistent with the present invention may include continuous injection of embolizing composition until it appears to flow towards an undesired location, waiting for a time to arrest the flow of embolizing composition and to promote flow to another location, then repeating the injection until the embolization is complete. Preferred compositions exhibit the property of solidification from the outside to the inside; thus, it is believed that pausing the injection promotes flow to another location because the distal end of the composition flow hardens before composition which is more proximate to the distal end of the catheter. Preferred devices for use in the method are the Titan-14 high pressure catheter system made by MicroTherapeutics, Inc., and a high pressure syringe activated by a precision injection control knob.

The following examples are illustrative of the application of the methods of the invention and are not intended to limit the scope of the invention in any way.

EXAMPLES

Example 1

The method using a strategy for embolization including continuous injection of embolizing composition until it appears to flow towards an undesired location, waiting for a time sufficient to permit arrest of the flow of embolizing composition and to promote flow to another location, then repeating the injection until the embolization is complete is demonstrated for treatment of aneurysms in a porcine subject. FIGS. 6-11 show fluoroscope images of the embolization of an aneurysm using the methods of the invention. The aneurysm had dimensions of a 14 mm height, 10 mm sac diameter, and a 6 mm neck diameter.

A formulation of the Onyx™ embolizing composition made by Microtherapeutics, Inc. with a viscosity at 40° C. of 1000 centistokes is used. The composition comprises EVOH as the biocompatible polymer, micronized tantalum powder as the contrast agent, and DMSO as the biocompatible solvent.

Figure 12:
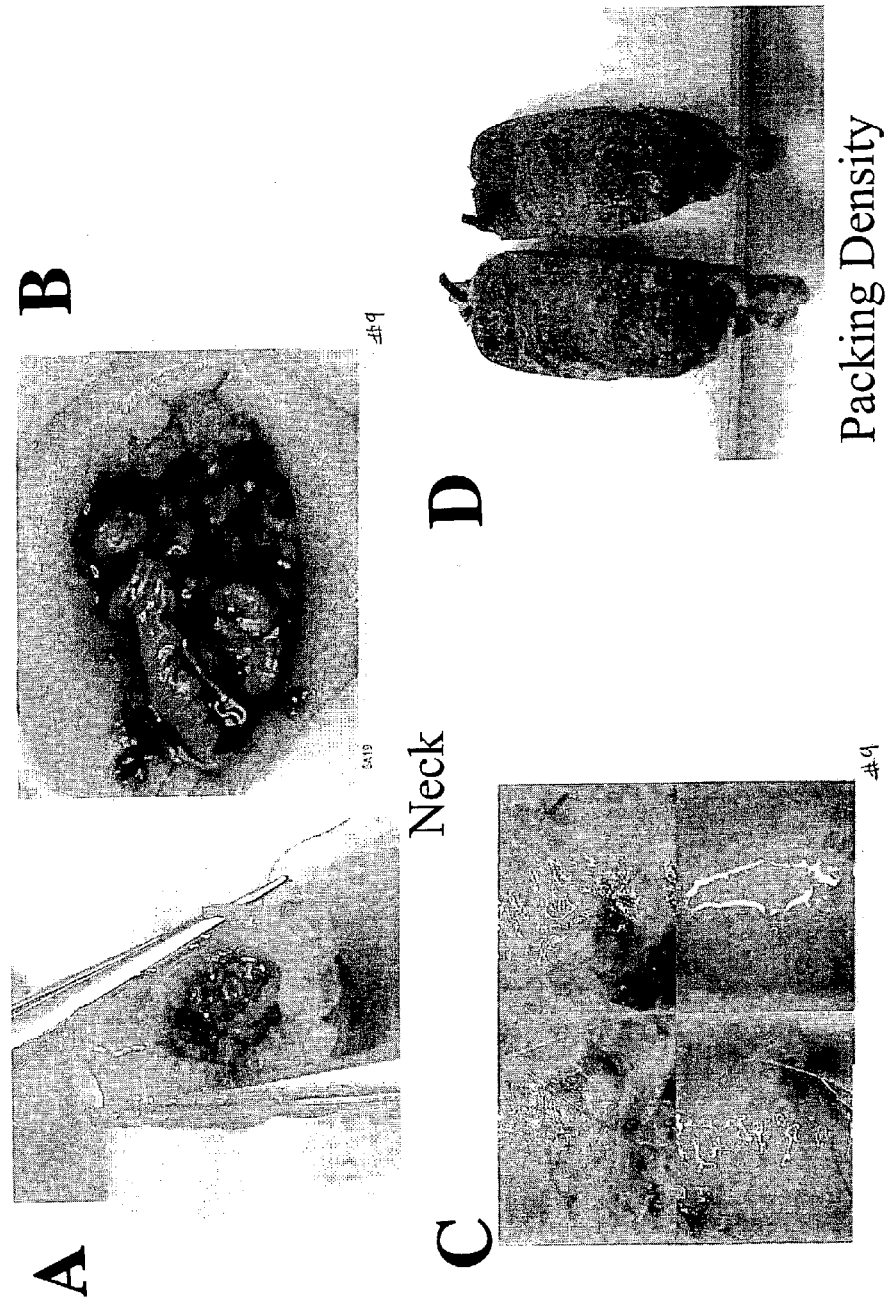
FIGS. 12(A-D) show dissections of the aneurysm filled in FIGS. 6-11.
Figure 13:
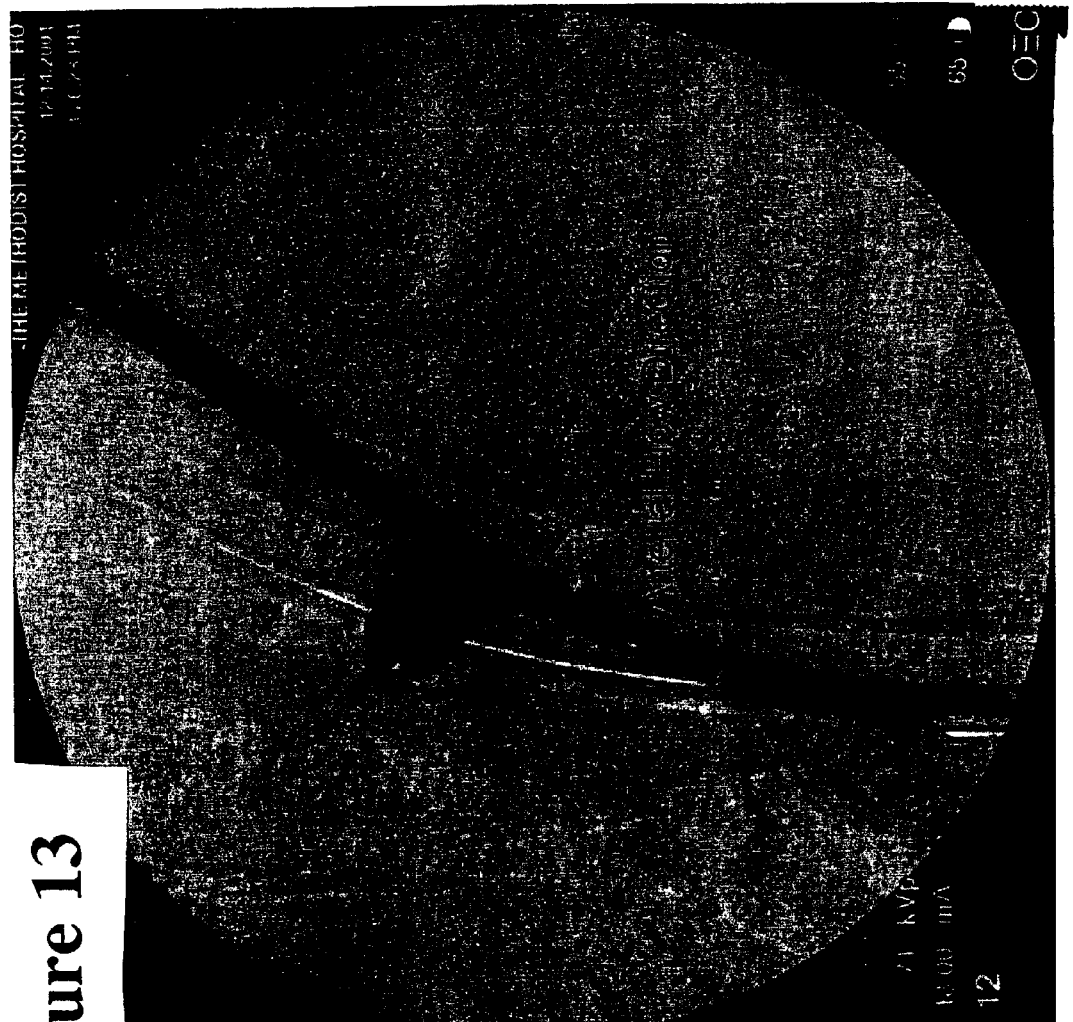
FIGS. 13-18 show fluoroscope images of the embolization of an aneurysm in a porcine subject. The embolizing composition of had a viscosity at 40° C. of 2500 centistokes. The aneurysm had dimensions 10 mm height, 10 mm sac diameter, and a 7 mm neck diameter.
Figure 14:
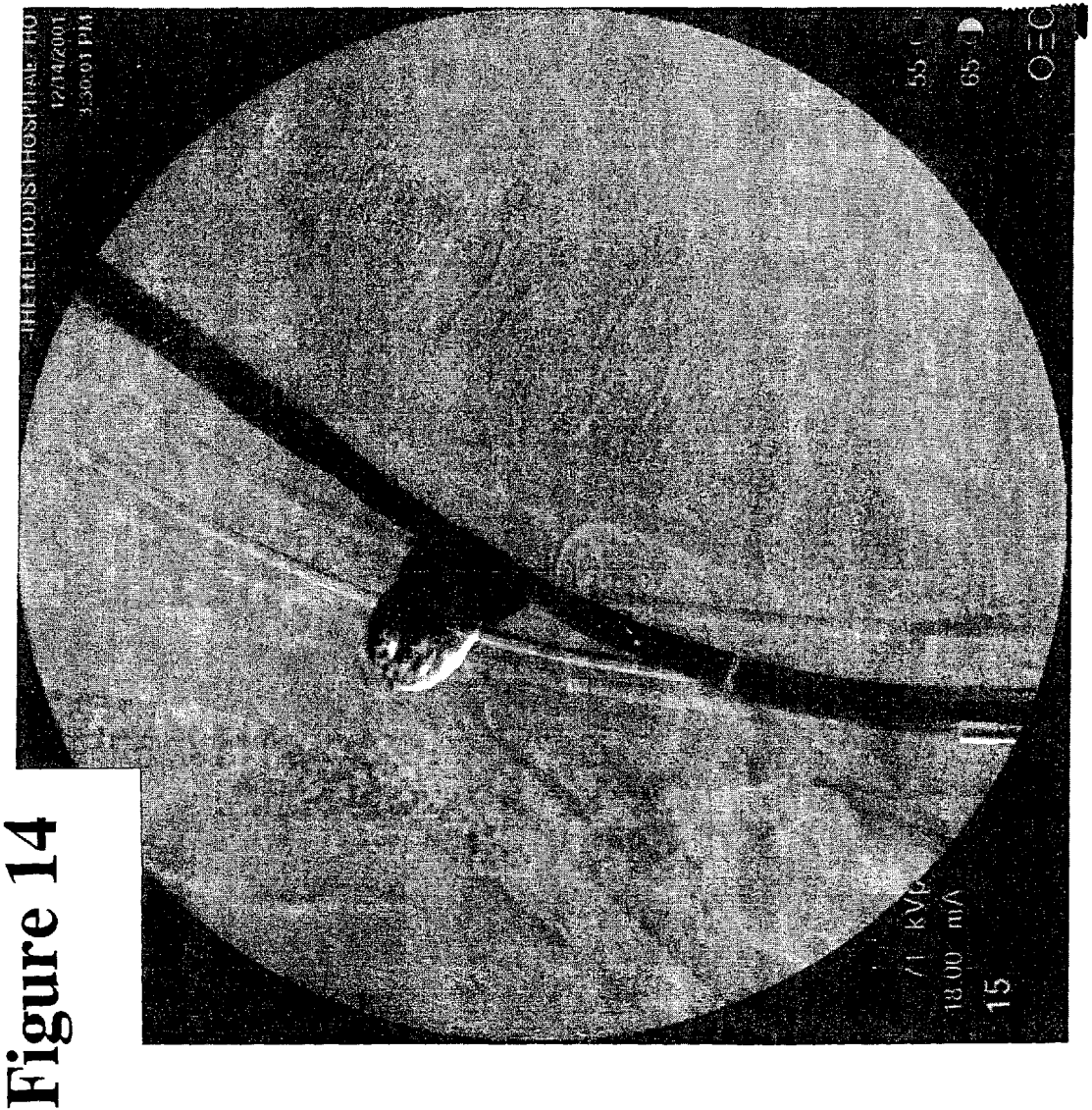
Figure 15:
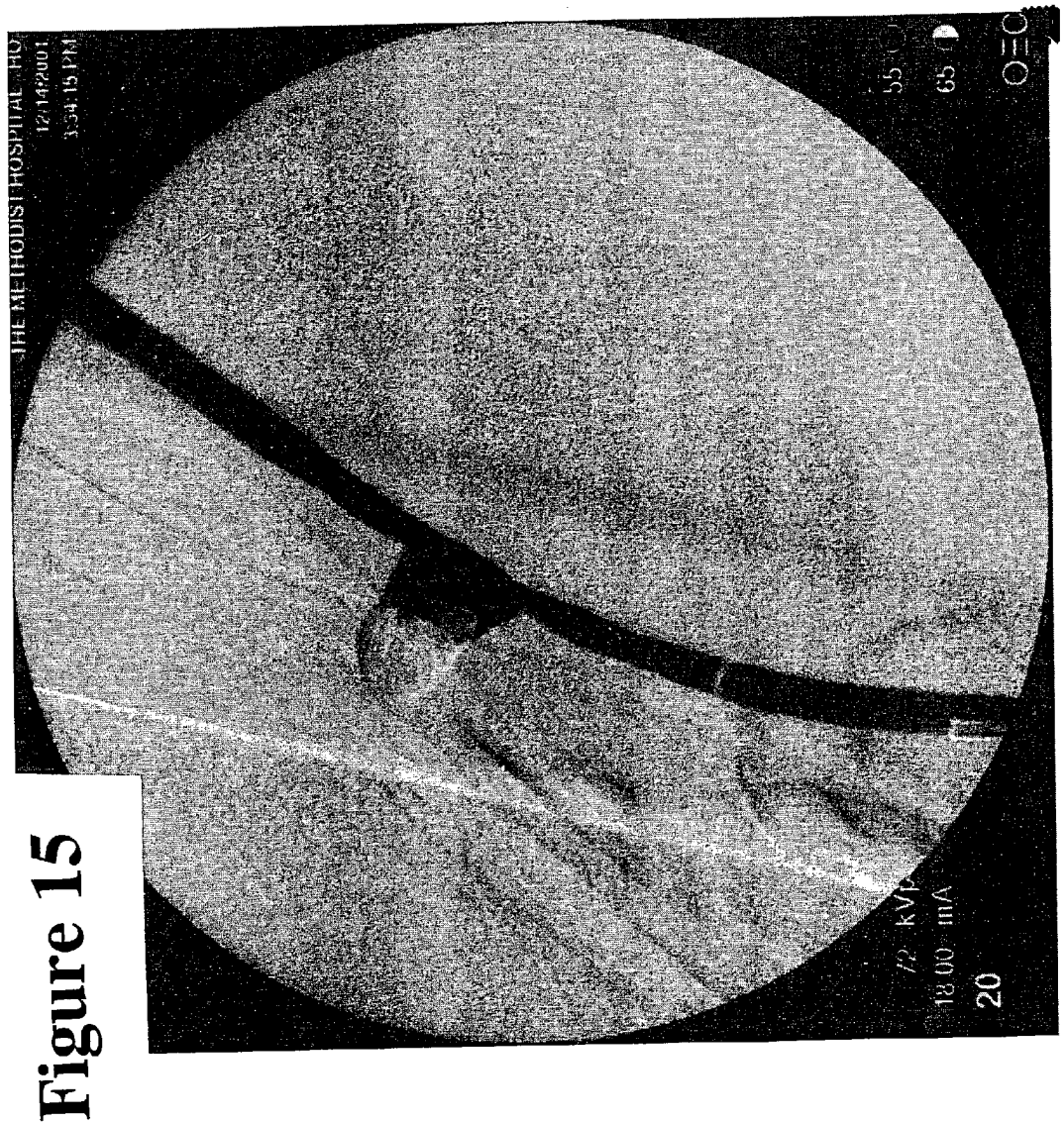
Figure 16:
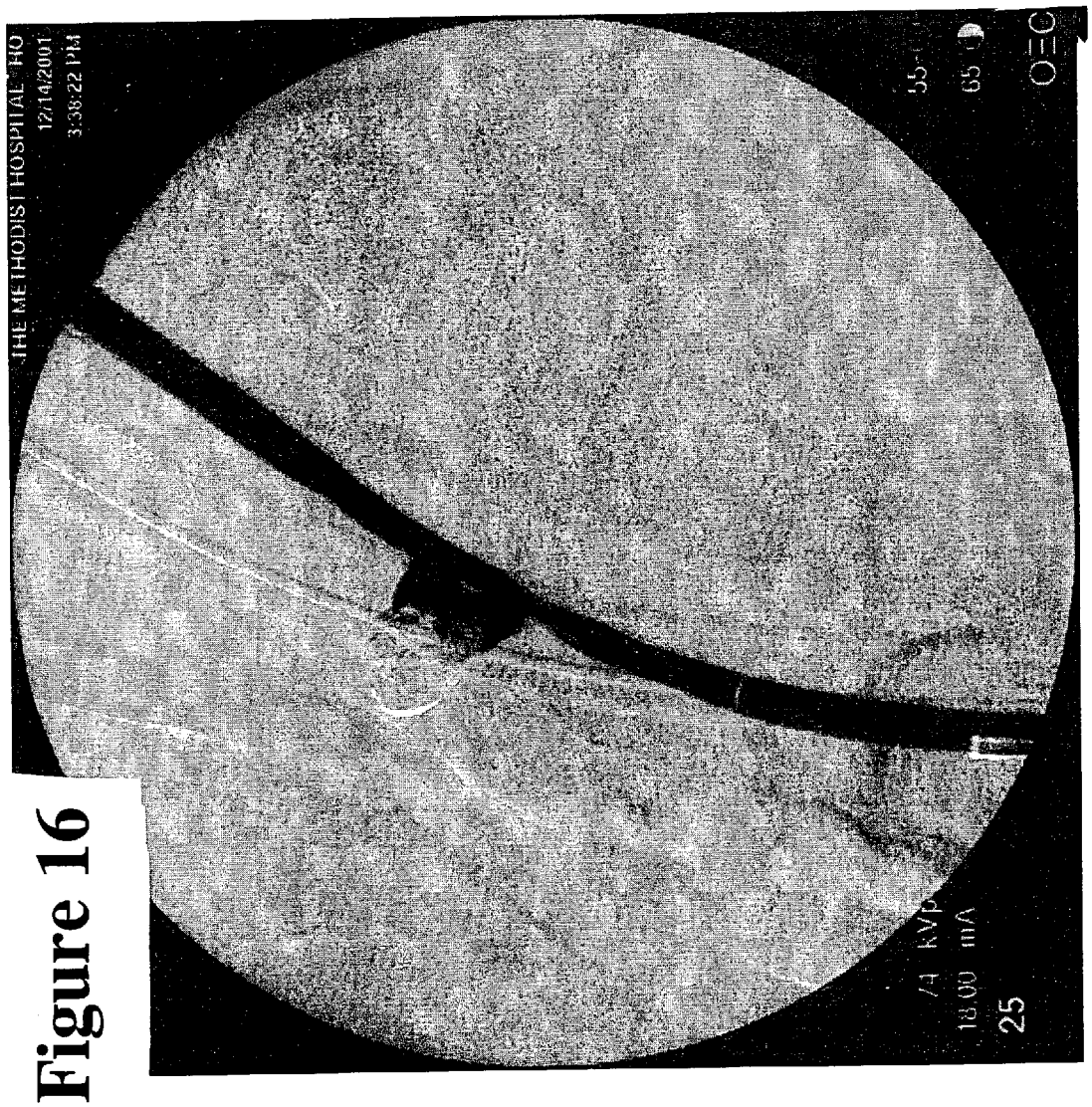
Figure 17:
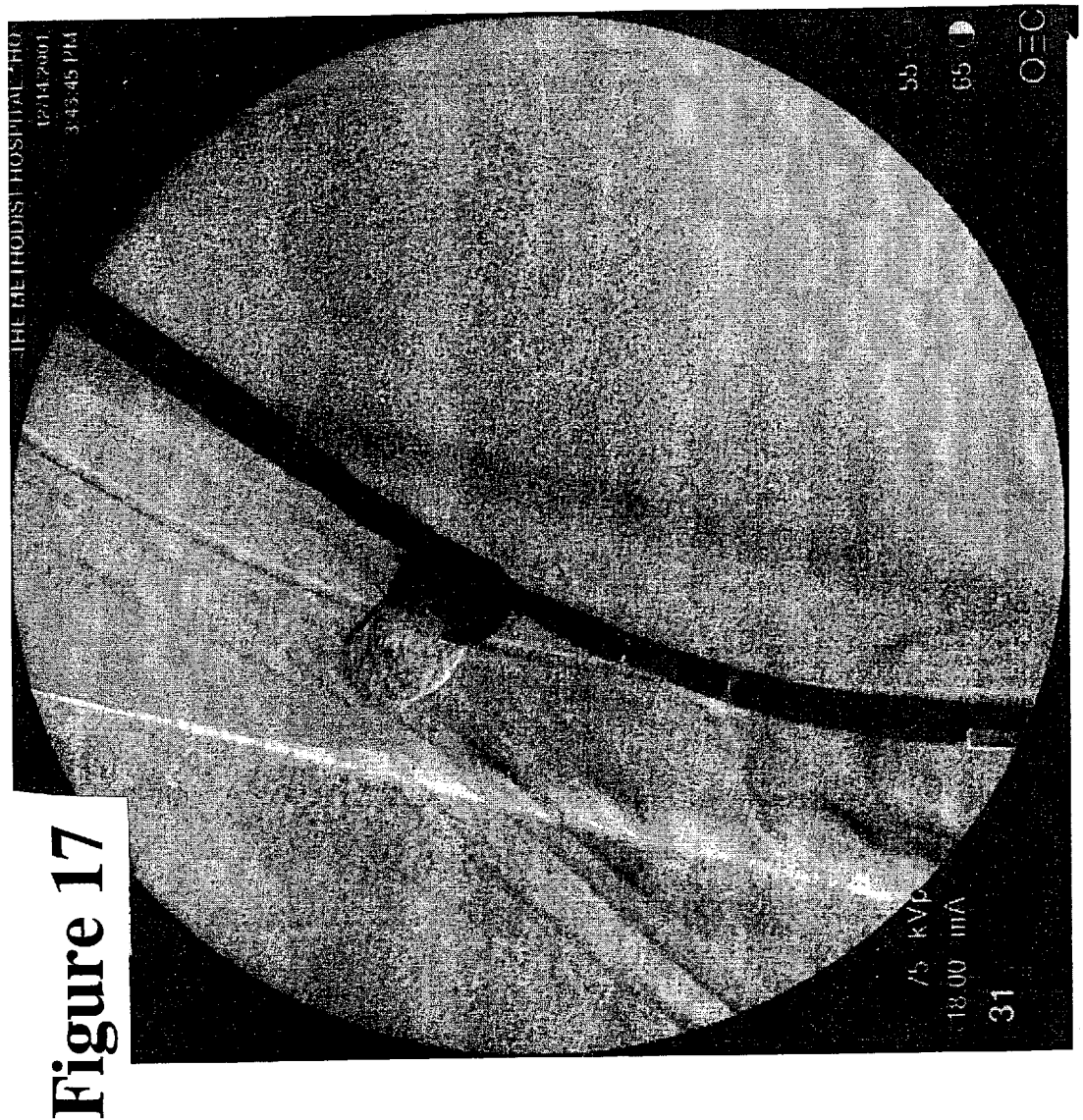
Figure 18:
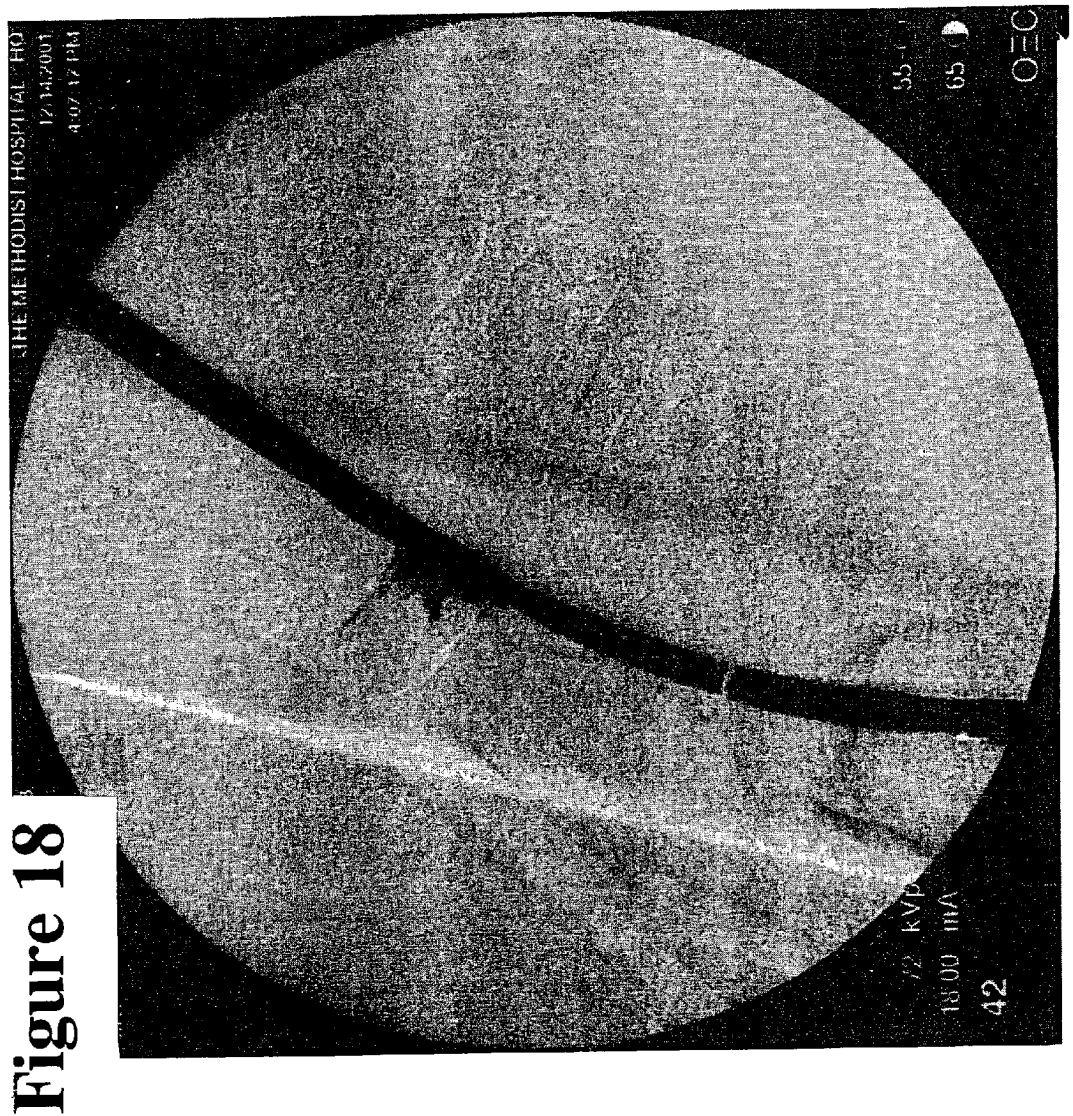

Injection according the methods of the invention takes place over the span of many minutes. The results are shown in FIGS. 12(A-D). As seen in FIGS. 12(A-C), the aneurysm is 98% filled, covering the in-flow zone with no protrusion of embolizing composition. The embolizing composition does not migrate and the parent artery remains open. As seen in FIG. 12(D), the mass is densely packed.

Example 2

As above, except that a formulation of the Onyx™ embolizing composition made by Microtherapeutics, Inc. with a viscosity at 40° C. of 2500 centistokes is used. FIGS. 13-18 show fluoroscope images of the embolization of an aneurysm. The aneurysm had dimensions 10 mm height, 10 mm sac diameter, and a 7 mm neck diameter.

Figure 19:
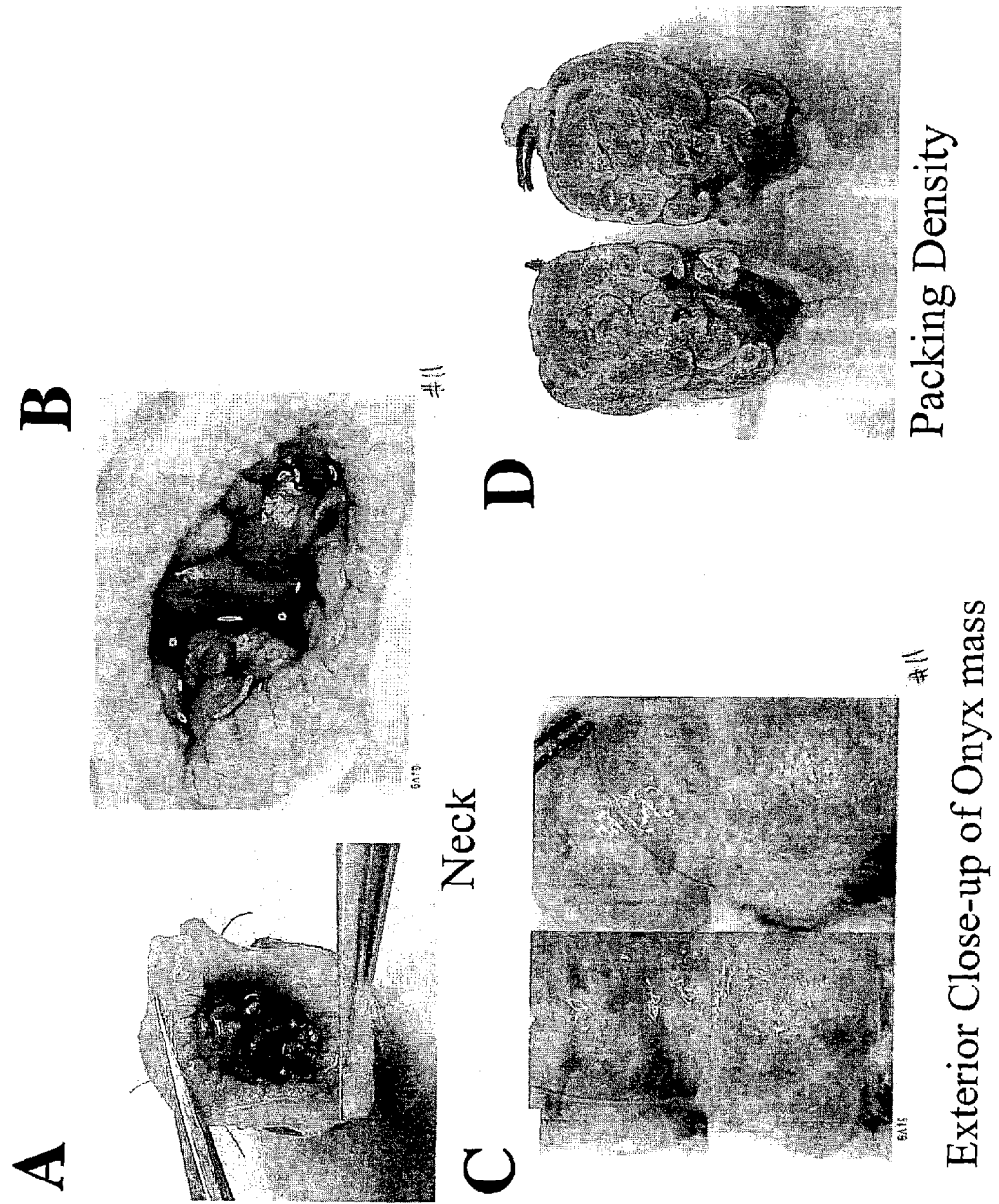
FIGS. 19(A-D) show dissections of the aneurysm filled in FIGS. 13-18.

Injection according the methods of the invention takes place over the span of many minutes. As seen in FIG. 19 (A-C), the aneurysm is 98% filled, covering the in-flow zone with no protrusion of embolizing composition. The embolizing composition does not migrate and the parent artery remains open. As seen in FIG. 19(D), the mass is densely packed.

While the invention has been described in detail with reference to preferred embodiments thereof, such as the treatment of vascular aneurysms, it will be recognized that the methods of the invention may be applied to the treatment of other vascular sites such as arterial venous fistulas within the scope of the invention. Further, it will be apparent to one skilled in the art that various changes can be made, and equivalents employed, without departing from the scope of the invention.

What is claimed is:

1. A method for embolizing a vascular aneurysm comprising an aneurysmal sac, an opening, and fundus by delivering to said vascular aneurysm via a catheter having proximal and distal ends a composition comprising (1) a biocompatible polymer; (2) a biocompatible water insoluble contrast agent; and (3) a biocompatible solvent, said method includes:

(a) positioning the distal end of said catheter in said vascular aneurysm wherein the proximal end of said catheter is connected to a source of said composition and whereby said composition can be injected into the vascular aneurysm through said catheter wherein the distal end of the catheter is positioned through the opening into the aneurysmal sac to be embolized about ⅔ of the distance between the opening and the fundus; and, (b) injecting an amount of said composition into the vascular aneurysm; and, (c) waiting a sufficient period of time to permit blood flow to transport biocompatible solvent away from the vascular aneurysm;

wherein steps (b) and (c) may be repeated until the vascular aneurysm is substantially filled, and wherein said composition has a viscosity at about 40° C. of greater than about 1000 centistokes, wherein no flow arresting device is activated during steps (b) and (c), and further wherein (d) after determining that the vascular aneurysm is substantially filled, activating a balloon capable of sealing the opening of the vascular aneurysm which is being embolized; and, (e) injecting a final amount of said composition into the vascular aneurysm such that the vascular aneurysm is completely filled with embolizing composition;

wherein the balloon is inflated in an arterial site to seal a neck of the vascular aneurysm that is about 100% to 130% of an inner diameter of a vascular vessel, and wherein no flow arresting device is activated during steps (b) and (c).

2. The method of claim 1, wherein the composition has a viscosity at 40° C. of about 1000 to about 20,000 centistokes.

3. The method of claim 1, wherein the composition has a viscosity at 40° C. of about 1000 to 4000 centistokes.

4. The method of claim 1, wherein the composition has a viscosity at 40° C. of about 2000 to 3000 centistokes.

5. The method of claim 1, wherein the composition has a viscosity at 40° C. selected from the group consisting of about 2300 centistokes, 2500 centistokes and 3200 centistokes.

6. The method of claim 1, wherein the composition has a viscosity such that a compact mass of embolizing precipitate is formed in the vascular aneurysm, in the form of a dense spheroid proximate to the distal end of the catheter.

7. The method of claim 1, wherein a pressure greater than the burst strength is not formed in any component of an apparatus through which the composition is delivered.

8. The method of claim 1, wherein the time waited in step (c) is sufficient to allow blood flow to transport biocompatible solvent away from the vascular aneurysm and is further sufficient to allow for precipitate formation.

9. The method of claim 1, wherein during the time of step (c), the extent to which the vascular aneurysm has been filled is determined.

10. The method of claim 1, further including a step, prior to step (b), injecting the biocompatible solvent into the catheter to fill a lumen of said catheter followed by injecting a first amount of said composition into said catheter whereby at least a portion of said biocompatible solvent is ejected from said catheter into the vascular aneurysm and washed downstream therefrom.

11. The method of claim 1, wherein injection in step (b) is continuous until the composition is observed to flow toward an undesired location and wherein the time in step (c) is sufficient to promote flow towards to another location unless the vascular aneurysm is substantially filled.

* * * * *